(12) United States Patent
Van Soolingen et al.

(10) Patent No.: US 6,245,934 B1
(45) Date of Patent: Jun. 12, 2001

(54) METHOD FOR PREPARING SALTS OF ASPARTAME FROM N-PROTECTED ASPARTAME

(75) Inventors: Jacob Van Soolingen, Brunssum; Wilhelmus H. J. Boesten, Sittard, both of (NL)

(73) Assignee: DSM NV, Heerlen (NL)

( * ) Notice: Subject to any disclaimer, the term of this patent is extended or adjusted under 35 U.S.C. 154(b) by 0 days.

(21) Appl. No.: 09/455,502

(22) Filed: Dec. 6, 1999

Related U.S. Application Data

(63) Continuation of application No. PCT/NL98/00296, filed on May 25, 1998.

(30) Foreign Application Priority Data

Jun. 6, 1997 (NL) .................................................. 1006243

(51) Int. Cl.⁷ .................................................. C07C 229/00
(52) U.S. Cl. .................................................. 560/41; 544/2
(58) Field of Search .................................. 560/41; 544/2

(56) References Cited

U.S. PATENT DOCUMENTS

| | | | |
|---|---|---|---|
| 3,492,131 | 1/1970 | Schlatter | 99/141 |
| 3,689,486 | 9/1972 | Clauss et al. | 260/243 R |
| 5,391,809 | 2/1995 | Takemoto et al. | 560/41 |
| 5,420,338 | 5/1995 | Takemoto | 560/41 |

FOREIGN PATENT DOCUMENTS

| | | |
|---|---|---|
| 0 294 860 | 12/1988 | (EP) . |
| 0 582 303 A1 | 2/1994 | (EP) . |
| 0 768041 A1 | 4/1997 | (EP) . |
| 2 140 805 | 12/1984 | (GB) . |

*Primary Examiner*—Howard C. Lee
*Assistant Examiner*—Leigh C. Maier
(74) *Attorney, Agent, or Firm*—Pillsbury Winthrop LLP

(57) ABSTRACT

Method for preparing a salt of aspartylphenylalanine methyl ester from N-protected aspartylphenylalanine methyl ester involving cleaving off the protective group by treatment with an acid, in the course of which, first of all, N-protected aspartylphenylalanine methyl ester is caused to react in an aqueous medium and in the presence of methanol at a temperature of from 0 to 80° C. with from 0.8 to 2 equivalents of acesulphamic acid for at least such a time that the conversion to the salt of aspartylphenylalanine methyl ester and acesulphamic acid has been completed to an adequate degree, and then the salt formed in the first step is isolated in precipitated form at a temperature of 30° C. or lower.

9 Claims, No Drawings

METHOD FOR PREPARING SALTS OF ASPARTAME FROM N-PROTECTED ASPARTAME

This application is a continuation of PCT/NL98/00296, filed May 25, 1998.

The invention relates to a method for preparing a salt of aspartylphenylalanine methyl ester from N-protected aspartylphenylalanine methyl ester involving cleaving off the protective group by treatment with an acid. The invention also relates, in particular, to a novel method for the deformylation of N-formylaspartylphenylalanine methyl ester by treatment with an acid.

Aspartylphenylalanine methyl ester, more in particular α-L-aspartyl-L-phenylalanine methyl ester (also known under the name of aspartame and hereinafter for the sake of convenience also abbreviated as APM), is used as a sweetener in foods and drinks, as described, for example, in the American patent U.S. Pat. No. 3,492,131. The sweetening power of aspartame is about 200× that of sugar; aspartame is thus considered one of the intense sweeteners. In various preparative routes of APM the amino group of the aspartic acid used as the starting material is protected by means of a group which can be cleaved off by treatment with an acid, for example by means of a formyl group (see e.g. GB-A-2140805), in order to achieve selective coupling of an acid group of aspartic acid and the amino group of phenylalanine (methyl ester). In the preparation of the sweetener APM it is important, moreover, not only that both amino acids in aspartame are present in the L-form, but also that the peptide bond is established to the α-carboxyl group of aspartic acid and not to the β-carboxyl group (i.e. with formation of α-APM and not β-APM). In chemical coupling processes of L-phenyl-alanine (methyl ester) and N-protected aspartic acid, for example N-formyl-aspartic acid (hereinafter also referred to as F-Asp) the aim therefore is at the coupling already to achieve the highest possible ratio α-APM/β-APM, and in subsequent process steps efforts are made to separate the A-APM selectively from the β-APM.

The preparation of a salt of aspartylphenylalanine methyl ester (APM) from N-protected APM by treatment with an acid, viz, oxalic acid, is disclosed by EP-A-0294860. In this case the oxalic acid salt of APM is obtained as a solid but as such, i.e. without further work-up to APM by neutralization (with recovery of oxalic acid), is of no further importance. The method in question, even though excellent yields are obtained and the formation of unwanted by-products such as the dimethyl ester of APM (abbreviated to $APM_2$) and/or diketopiperazine (DKP) is generally low, moreover has the drawback that it is necessary to work at relatively low concentrations (i.e. usually less than 15 wt % of N-protected starting material to be treated) in a special solvent combination of methyl isobutyl ketone and methanol, at relatively high temperatures, e.g. from 30 to 60° C., after which the salt is worked up by cooling, washing etc. Complete removal of the strongly odorous methyl isobutyl ketone from the salt obtained proves difficult in this process.

There is therefore a need for an alternative method for preparing a salt of APM from N-protected APM, in particular from the corresponding N-formyl compound (hereinafter also referred to as F-APM), by treatment with an acid, which does not have the abovementioned drawbacks.

Surprisingly, it now has been found that N-protected APM can be converted in a simple manner into a salt if in a first step, N-protected aspartylphenyl-alanine methyl ester is caused to react in an aqueous medium and in the presence of methanol at a temperature of from 0 to 80° C. with from 0.8 to 2 equivalents of acesulphamic acid for at least such a time that the conversion to the salt of aspartylphenylalanine methyl ester and acesulphamic acid has been completed to an adequate degree, and in a second step the salt formed in the first step is isolated in precipitated form at a temperature of 30° C. or lower.

Acesulphamic acid is an organic sweetening acid corresponding to an intense sweetener not derived from aspartic acid, namely acesulphame-K. Acesulphame-K (6-methyl-1,2,3-oxathiazin-4(3K)-one-2,2-dioxide; hereinafter also referred to as AceK) has a sweetening power which is approximately 200× that of sugar. This intense sweetener is disclosed inter alia by U.S. Pat. No. 3,689,486. Acesulphamic acid (hereinafter also referred to as AceH) can be represented chemically as 6-methyl1,2,3-oxathiazin-4(3H)-one-2,2-dioxide.

The method according to the invention can, if desired, also be implemented in the presence of a mineral acid, for example hydrochloric acid, sulphuric acid or phosphoric acid. The amount of such an additionally present mineral acid may vary within wide limits, but will usually not exceed 0.5 molar equivalents with respect to the acesulphamic acid. The conversion according to the method of the invention can already be carried out, however, with particularly good results even without an additional amount of a mineral acid being present.

Other organic sweetening acids corresponding to intense sweeteners not derived from aspartic acid (hereinafter also simply referred to as organic sweetening acids) are known, but if they are used in the manner as described within the scope of the present invention for AceH, they behave in an entirely different manner and are therefore not suitable for use within the scope of the present invention. This is particularly surprising. Such other organic sweetening acids include, for example, the corresponding acids of other intense sweeteners currently available, which are derived not from aspartic acid but from other organic acids. An example of such an organic sweetening acid which cannot be used within the scope of the present method is saccharinic acid (the acid corresponding to saccharin-Na, i.e. sodium 2,3-dihydro-3-oxo-benzisosulphonazole; 300× sugar). As is known, the sodium, calcium and potassium salts in particular of the said organic sweetening acids have sweet properties.

The acesulphamic acid (AceH), which is used as an organic sweetening acid within the scope of the present invention, can be employed in the form of the respective free acid (6-methyl-1,2,3-oxathiazin-4(3H)one-2,2-dioxide), or alternatively be formed in situ (or possibly beforehand) by the corresponding potassium, sodium or calcium salt being treated with an at least equivalent amount of an inorganic mineral acid, e.g. hydrochloric acid, sulphuric acid or phosphoric acid. Most convenient, of course, is the preparation from AceK.

According to the method of the invention, the deprotection reaction involves formation of the salt of APM and AceH, hereinafter also referred to as APM.Ace. As disclosed by EP-A-0768041, salts of APM and organic sweetening acids and in particular of AceH, have excellent sweetening properties, and such salts (sweetening salts) can, like APM, be suitably used for sweetening foods such as soft drinks, dietary products, chewing gums, confectionery, sweets, etc.

If, within the scope of the method of the present invention, AceH is to be prepared beforehand, this can be effected in a very suitable manner by a reslurrying process, in analogy to the method described in EP-A-0768041 for preparing salts of APM and organic sweetening acids, on the understanding that the method in question is implemented without APM being present.

The method according to the present invention preferably employs AceH prepared in situ.

According to the method of the invention, the salt of APM and AceH, i.e. APM.Ace, which is particularly suitable as a sweetener, is formed in all cases.

The N-protected APM used can be any N-protected APM in. which the protective group can be removed by treatment with acid. Examples of N-protected APM are N-formyl-APM (F-APM), N-t-butyloxycarbonyl-APM and Dane salts of APM (these are products formed by coupling phenylalanine methyl ester to aspartic acid protected by means of a Dane group, i.e. aspartic acid in which the amino group has first reacted with an ester of acetoacetic acid, e.g. the octyl or octadecyl ester thereof, see e.g. EP-A-0143881).

The N-protected APM used is preferably N-formyl-APM (F-APM). Deprotection of F-APM, in particular of product which, in addition to α-APM also contains up to e.g. 30 wt % of F-β-APM, with the aid of mineral acids, e.g. hydrochloric acid, is one of the most important processes currently used commercially for the preparation of aspartame, the ultimate result of which, after neutralization of the mineral acid salt formed in the course of the deprotection, is that α-APM is obtained solely or at any rate predominantly, i.e. >95 wt % (on the basis of the dry weight). The present invention provides a very suitable alternative for such deprotection, in particular if it is intended to convert it, in a subsequent step, by deprotection of F-APM, into e.g. APM.Ace. The fact is that thus, starting from F-APM, a simple single-step process is obtained for the preparation of the product APM.Ace, which is particularly suitable as a sweetening salt. Such a single-step process starting from N-protected APM has not been known up till now.

In this context it is also worth mentioning that even the conversion of F-APM to APM according to the prior art proceeds via a multistep process, i.e. via the formation of the HCl salt of APM and APM being obtained therefrom by neutralization etc. This means that, given the prior art, the formation of a suitable sweet product (i.e. APM) from F-APM proceeds via a multistep process. The method according to the invention now achieves a single-step process to the formation of a suitable sweet product (i.e. APM.Ace).

A particular advantage in this context of the method of the present invention is that the APM.Ace obtained by precipitation, even if the starting material is a mixture of α-APM and β-APM (comprising the β-form, for example, in a percentage by weight of up to 30 %) consists entirely or virtually entirely, i.e. to more than 95 %, often about 98 wt % (on the basis of dry weight) of α-APM.Ace.

The conversions in question can be carried out at high concentrations of the starting materials (N-protected APM and AceH or salt thereof). They can even take place under conditions at which one or more of the starting materials and the ultimately formed salt, at least in part, are present in solid form. Thus the APM.Ace formed can be obtained in a high volume yield. During the course of the conversion a homogeneous system is often involved, in which all the components present are dissolved, but from which the APM.Ace can be precipitated, certainly once the conversion has been completed to an adequate degree.

The term 'aqueous medium', within the context of the present application, refers to any reaction medium whose liquid phase mainly consists of water and possibly a limited amount, e.g. up to at most about 40 wt % of the amount of water, of methanol. With the method according to the invention it is desirable that at least a small amount of methanol be present in the reaction system, since as a result the unwanted effects of any hydrolysis which may occur of the ester group in the APM moiety are minimized. The presence of methanol moreover enhances the solubility of the N-protected APM, in particular of the F-APM, in the reaction medium, which has a beneficial effect on the rate of the deprotection reaction, e.g. the deformylation reaction. The presence of one or more other solvents, which may or may not be miscible with water, is not desirable from the point of view of process advantages, but need not be precluded if the solvents in question show inert behaviour under the reaction conditions with respect to the reactants and the end product.

The temperature at which the conversion according to the invention is carried out can be adjusted within wide limits, for example between 0 and 80° C., but it is preferable (and that is a particular advantage of the present method) for the conversion suitably to be carried out at temperatures below 30° C. Under such conditions the formation of by-products or secondary products is negligibly small. The precipitated APM.Ace will usually be isolated at a temperature of 30° C. or less. The higher the amount of methanol present in the reaction system, the higher, also, will be the solubility of the APM.Ace formed and it will be preferable to carry out the precipitation thereof at even lower temperatures, e.g. below 20° C. As a result of the precipitation of APM.Ace, the equilibria of various reactions which might lead to the formation of by-products (such as e.g. the formation of the dimethyl ester of APM, the formation of the demethylated product aspartylphenylalanine (AP), or the formation of a product in which the ester group is bound in the aspartyl moiety instead of to the phenyl-alanine group (AMP)) are advantageously shifted, which further increases the yield of APM.Ace.

The conversion according to the invention usually as a rule takes place under conditions such that the amount of acesulphamic acid used is from 0.8 to 2 equivalents (expressed in moles) with respect to the amount of N-protected APM used. This means that both the N-protected APM and the organic sweetening acid may be present in slight (and acesulphamic acid even up to molar) excess. of course the conversion according to the invention proceeds even if the molar ratio of acesulphamic acid to N-protected APM is outside this range of from 0.8:1 to 2:1, but in these cases the solid product present at the end of the reaction may contain not only the APM.Ace formed which—given a sufficiently long conversion time—is present in a relatively large amount, at most corresponding to the molar amount of the substoichiometrically present starting material (and as regards N-protected APM only insofar it is present in the form of N-protected α-APM), but may also contain some of the starting material present in excess. The latter is of course less desirable. Within the ratios mentioned of starting materials, however, usually only, or at least predominantly, i.e. more than 95 wt % (on the basis of dry weight) of, APM.Ace will be present in the precipitate. Attainment of the point in time at which the conversion to the salt of APM and AceH has been completed to an adequate degree can be established in a simple manner by the reaction mixture being sampled and analysed with the aid of thin-layer chromatography (TLC), particular attention being given to the formation of α-APM (and in particular of α-APM.Ace) and to the disappearance (in the case of successive sampling) of the products which contain a formyl group (such as F-APM, F-AP and F-APM$_2$) and to the disappearance of undesired by-products such as AP, APM$_2$ and AMP, and to the slow disappearance of β-APM.Ace. The conversion can be regarded as having been completed to an adequate degree if the TLC analysis indicates virtually no residual undesirable by-products. Analysis of the precipitate isolated at the end of the conversion, in particular after the precipitation at a temperature of 30° C. or less, can then (after washing and drying) be effected in a simple manner with the aid of high-pressure liquid chromatography (HPLC), which provides a more quantitative picture of the results achieved. According to the method of the invention a precipitate is obtained, usually, the APM.Ace of which consists of at least 98 wt % (based on dry material) of α-APM.Ace.

The conversion is preferably carried out over such a time, depending inter alia on temperature, concentrations of starting materials, composition of the reaction system and the like (which is readily determined by those skilled in the art in accordance with the directions from the present patent application), that the conversion of the starting material (possibly) present in a substoichiometric amount is virtually complete. The duration of the conversion often is many days, e.g. from 3 to 10 days, before the end of the conversion is attained.

The solid APM.Ace isolated at the end of the reaction, after completion of the precipitation at a temperature of 30° C. or less, by solid-liquid separation, via any method known to those skilled in the art and suitable for this purpose can then additionally in a simple manner be washed with, for example, cold water and be dried. Washing and drying can be achieved by any of the methods known to those skilled in the art.

The invention is explained below with reference to a number of examples and comparative examples without, however, being limited to the precise embodiments and conditions of the examples.

In the TLC analyses carried out within the context of the experiments (regarding both the preparation of F-APM and the conversion to APM.Ace or the deprotection of F-APM) the eluent used was a mixture of sec-butanol+formic acid+water in a respective volume ratio of 75:15:10 (v/v/v). Confirmation of the presence or absence of the formyl protective group in the products separated via TLC was furthermore obtained by the TLC plates after drying being sprayed with a ninhydrin solution, the unprotected products containing a free primary amino group producing discoloration.

The HPLC method also used was carried out at 22° C. with the aid of a Hewlett Packard type 1081B liquid chromatograph equipped with a Nucleosil C18 column and UV detection (in a flow cell, at 210 nm) the eluent used being a fresh aqueous phosphate buffer of pH=3.00, which contained about 10 wt % of acetonitrile.

EXAMPLE I

Preparation of APM.Ace from F-α-APM and AceH a) Preparation of F-α-APM

F-α-APM was prepared by 30 g of α-APM (0.1 mol) in 46 g of formic acid being treated at room temperature with 20.4 g of acetic anhydride (0.2 mol). The reaction was monitored by means of TLC. After quantitative formylation of the free amino group had been achieved, the mixture obtained was then boiled down under reduced pressure to a small volume, the precipitate obtained was filtered and washed (with diethyl ether) and finally dried in vacuo. The yield was about 32 g of F-α-APM (according to $^1$H-NMR analysis >95%).

b) Deprotection of F-α-APM with the formation of APM.Ace 3.3 g (10 mmol) of the F-α-APM obtained in a) were taken up in a mixture of 4.0 ml of water and 1.0 ml of methanol, and then 3.3 g of AceH (20 mmol) were added. An initially clear solution was obtained which, with stirring for 3 days at about 25 to 30° C., was gradually converted into a suspension. After said 3 days' stirring, the suspension was cooled to 5° C., and the precipitated product was then filtered off, washed with 2.0 ml of ice water and dried in a vacuum oven at 50° C. The white microcrystalline substance thus obtained (1.40 g, i.e. 3.1 mmol) was characterized, with the aid of TLC and $^1$H-NMR, as the salt of α-APM and AceH, APM.Ace, having a purity of more than 95 wt %. Analysis of the reaction mixture filtered off and the precipitate obtained further showed that deformylation of the F-α-APM used as a starting material was complete, without significant amounts of unwanted by-products having been formed, such as the a-AP formed by demethylation of α-APM or as DKP.

EXAMPLE II

Preparation of α-APM.Ace from F-α/β-APM and AceH(formed in situ) in the presence of mineral acid a) Preparation of F-α/β-APM F-α/β-APM was prepared by a solution of 18 g of L-phenyl-alanine methyl ester (0.1 mol) in 200 ml of toluene being added dropwise over a period of about 30 minutes to a suspension of 15 g of N-formylaspartic anhydride (0.1 mol) in 50 ml of glacial acetic acid. To the suspension thus obtained, a further 300 ml of toluene were then added, and all of this was then boiled down under reduced pressure (water-jet pump) at 50° C. The yield of solid residue was about 33 g (which, according to TLC analysis was found to consist quantitatively, i.e. in a total of 0.1 mol, of a mixture of F-α-APM and F-β-APM in a weight ratio of about 80:20).

b) Deprotection of F-α/β-APM with the formation of APM.Ace

The solid residue from a) was taken up in a mixture of 35 g of water and 5 g of methanol. This was successively admixed with 21 g (0.1 mol) of the potassium salt of AceH (AceK) and 12 g of a 37 wt % aqueous solution of hydrochloric acid (0.15 mol of HCl). This produced a clear solution. The solution was stirred for 7 days at from 25 to 30° C., a suspension being formed. The suspension was then thickened in 3 hours, with the aid of a nitrogen flow, to about 80% of the original volume. The solid was filtered off and the residue was washed with 10 ml of ice water and dried in vacuo at 50° C. The white, microcrystalline solid (15 g, i.e. a yield of about 41% in terms of the originally present F-α-APM) was characterized as α-APM.Ace and had a purity of 97.9%. HPLC analysis moreover indicated that the presence of by-products in the solid was very slight (F-α-APM <0.2 wt %, β-APM about 0.2 wt %; DKP <0.2 wt %, AP about 0.8 wt %). Analysis of the reaction mixture filtered off and the precipitate obtained further showed that the deformylation of the F-α-APM used as a starting material was complete, without significant amounts of unwanted by-products having been formed, such as the α-AP formed by demethylation of α-APM or such as DKP.

Comparative Example A

Conversion of F-α-APM with saccharinic acid.

The method of Example I was repeated, except that in step b), instead of the AceH, 3.7 g of saccharinic acid (20 mmol)

were used. After 3 days' stirring, the solid present was filtered off, washed and dried (4.5 g in total). According to HPLC analysis this was found to consist of about 45 wt % of F-α-AP and about 47 wt % of saccharinic acid. Considerable demethylation was therefore involved. Moreover, formation of DKP amounted to about 1 wt % of the solid. AP was present in an amount of about 0.6 wt %.

Comparative Example B

Treatment of F-α/B-APM with saccharinic acid (formed in situ) in the presence of mineral acid The method of Example II was repeated, except that in step b), instead of the potassium salt of AceH, 23 g of sodium saccharinate (0.1 mol) were used. After 7 days' stirring, the solid present was filtered off, washed and dried (18 g, containing about 25 wt % of moisture, in total). According to HPLC analysis this was found to consist of about 9.5 wt % of F-α-APM and about 61 wt % of saccharinic acid. only 0.2 wt % of DKP was found.

What is claimed is:

1. A method for preparing a salt of aspartylphenylalanine methyl ester from N-protected aspartylphenylalanine methyl ester involving cleaving off the protective group by treatment with an acid comprising:

a) reacting N-protected aspartylphenylalanine methyl ester, in an aqueous medium and in the presence of methanol at a temperature of from 0 to 80° C., with from 0.8 to 2 equivalents of acesulphamic acid for at least such a time that the conversion to the salt of aspartylphenylalanine methyl ester and acesulphamic acid has been completed to an adequate degree, and b) precipitating the salt formed in step (a) at a temperature of 30° C. or lower.

2. The method according to claim 1, wherein said N-protected aspartylphenylalanine methyl ester is reacted in the presence of a mineral acid selected from the group consisting of hydrochloric acid, sulphuric acid or phosphoric acid, in an amount of at most 0.5 molar equivalents with respect to the acesulphamic acid.

3. The method according to claim 1 wherein said acesulphamic acid is formed in situ by a corresponding potassium, sodium or calcium salt being treated with an at least equivalent amount of a mineral acid selected from the group consisting of hydrochloric acid, sulphuric acid or phosphoric acid.

4. The method according to claim 1 characterized in that N-formyl-aspartylphenylalanine methyl ester is used as the N-protected-formylaspartylphenylalanine methyl ester.

5. A method for deprotecting N-formylaspartylphenylalanine methyl ester, comprising:

a) reacting N-formylaspartylphenylalanine methyl ester, in an aqueous medium and in the presence of methanol at a temperature of from 0 to 80° C., with from 0.8 to 2 equivalents of acesulphamic acid for at least such a time that the conversion to the salt of aspartylphenylalanine methyl ester and acesulphamic acid has been completed to an adequate degree, and b) precipitating the salt formed in the first step at a temperature of 30° C. or lower.

6. A method according to claim 1 wherein said reaction is carried out at a temperature of 0 to 30° C.

7. A method according to claim 1 wherein said N-protected aspartylphenylalanine methyl ester used is a mixture of N-formyl-$_\alpha$- and N-formyl-$_\beta$-aspartylphenylalanine methyl ester, the amount of N-formyl-$_\beta$-aspartylphenylalaninemethyl ester being at most 30 wt % with respect to the total of N-formyl-$_\alpha$- and N-formyl-$_\beta$-aspaspartylphenylalanine methyl ester.

8. A method according to claim 5 wherein said reaction is carried out at a temperature of 0 to 30° C.

9. A method according to claim 5 wherein said N-protected aspartylphenylalanine methyl ester used is a mixture of N-formyl-$_\alpha$- and N-formyl-$_\beta$-aspartylphenylalanine ester being at most 30 wt % with respect to the total of N-formyl-$_{60}$- and N-formyl-$_\beta$-aspartylphenylalanine methyl ester.

\* \* \* \* \*